US00PP14323P29

(12) United States Plant Patent
Hanes

(10) Patent No.: US PP14,323 P2
(45) Date of Patent: Nov. 25, 2003

(54) PETUNIA PLANT NAMED 'WHIP LITYEL'

(50) Latin Name: *Petunia hybrida*
Varietal Denomination: Whip Lityel

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,095
(22) Filed: Mar. 13, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by light yellow colored flowers, compact habit and good basal branching.

1 Drawing Sheet

Genus and species: *Petunia hybrida.*
Variety denomination: 'Whip Lityel'.

BACKGROUND OF THE NEW PLANT

The present invention comprises a new and distinct cultivar of petunia, botanically known as *Petunia hybrida,* and hereinafter referred to by the cultivar name 'Whip Lityel'. The new cultivar is asexually reproduced from vegetative cuttings and tissue culture resulting from the cross of the seed/pod parent 99-296-3, a light yellow proprietary line that is unnamed and unpatented×99-264-4, a purple with a yellow throat proprietary line that is unnamed and unpateneted.

'Whip Lityel' is a product of a planned breeding program intended to create new petunia plants with Light yellow colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Whip Lityel'. The data, which defines these characteristics, were collected from asexual reproductions carried out in Gilroy, Calif. The plant history was taken on 6 months old plants grown in one-gallon pots in fall/winter season, in a poly-covered greenhouse under 2–4 hours supplemental light and color readings were taken in the greenhouse in the winter season under natural light.

Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms: Approximately 5–10 cm.
Width: Approximately 50–60 cm including flowers.
Time to produce a finished flowering plant: 9–11 weeks.
Outdoor plant performance: Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 3.5–4.0 cm.
Width: 1.7–2.2 cm.
Leaf blade shape: Elliptic.
Leaf margin: Entire.
Apex aspect: Rounded.
Base aspect: Acuminate.
Leaf color: Upper side; RHS 137A (green); Underside; RHS 137C/D (green).
Texture: Sparse glandular hairs of various sizes.
Venation: Palmate.
Venation color: RHS 144A (yellow-green).
Petiole length: 0.8–1.0 cm.
Petiole width: 0.15–0.2 cm.
Petiole color: RHS 144A (yellow-green) but a little greener.
Petiole texture: Sparse glandular hairs of various sizes.

THE STEM

Length: 30–40 cm.
Diameter: 0.2–0.3 cm.

Internode length: 0.5–1.5 cm.
Color: RHS 144A (yellow-green).
Texture: Very sparse long glandular hairs.
Stem anthocyanin: None.
Peduncle color: RHS 144A (yellow-green) but a little greener.
Peduncle length: 2.1–3.4 cm.
Peduncle diameter: 0.15 cm.
Peduncle texture: Many glandular hairs of various sizes.

THE BUD

Shape: Oblong.
Diameter: 0.5 cm.
Length: 1.0–2.0 cm.
Color at tight bud: RHS 144C (yellow-green).

THE FLOWER

Blooming habit: Continuous all through the growing season. Good floriferousness.
Inflorescence type: Flowers solitary in upper leaf axis.
Young flower color: RHS 155B (white) base color; RHS N144C (yellow-green) mid-veins with color bleeding into the petals; RHS 7B/C (yellow) and RHS 151B (yellow-green) secondary veining.
Young flower floret diameter: 3.0–3.4 cm.
Mature flower color: Front side, RHS 155A (white), base color; RHS N144C (yellow-green) mid-veins, color bleeds less into petals; RHS 7B/C (yellow) and RHS 151B (yellow-green) Secondary Veining. Underside, RHS 155C (white), base color; RHS 145A (yellow-green) mid-veins; subdued hue of RHS 151C (yellow-green) secondary veins.
Corolla color inside: RHS 155B (white) base color; RHS N144C (yellow-green) mid-veins; RHS 7B (yellow) heavy secondary veining.
Corolla length: 2.5–2.7 cm.
Corolla outside texture: Many glandular hairs of various sizes.
Floret form and number of petals: Funnel form, 5 lobed petals fused at base.
Flower (limb) diameter: 3.9–4.4 cm.
Petal apex shape: Pracmorse.
Petal base shape: Fused.
Petal margin: Entire.
Waviness of petals: Weak.
Petal lobation: Moderate.
Petal texture: Papillose.
Sepals: 5.
Sepal color: RHS 137A (green).
Sepal length: 1.6–1.8 cm.
Sepal width: 0.35–0.4 cm.
Sepal shape: Oblong.
Sepal apex: Acute.
Sepal texture: Many glandular hairs of various sizes.
Lastingness of individual blooms: 4–8 days.
Fragrance: None.

THE REPRODUCTIVE ORGANS

Stamens: Five, 2 taller and 3 shorter.
Filament color: RHS 155C (white).
Pollen color: RHS 11C (yellow).
Pistil: One.
Stigma: RHS 143C (green).
Style color: RHS 145D (yellow-green).
Fruit seed set: Not observed.

DISEASE AND INSECT RESISTANCE

Not observed.

COMPARISON WITH KNOWN CULTIVARS

Compared to its female parent 99-296-3 as follows: The female parent has a lighter yellow flower color on a plant that is later to flower than the 'Whip Lityel'.

Compared to its male parent 99-264-4 as follows: The male parent has a flower color that is purple with a yellow throat compared to the 'Whip Lityel', which has a light yellow flower. The male parent also has darker leaves than does the 'Whip Lityel'.

I claim:

1. A new and distinct petunia plant as shown and described herein.

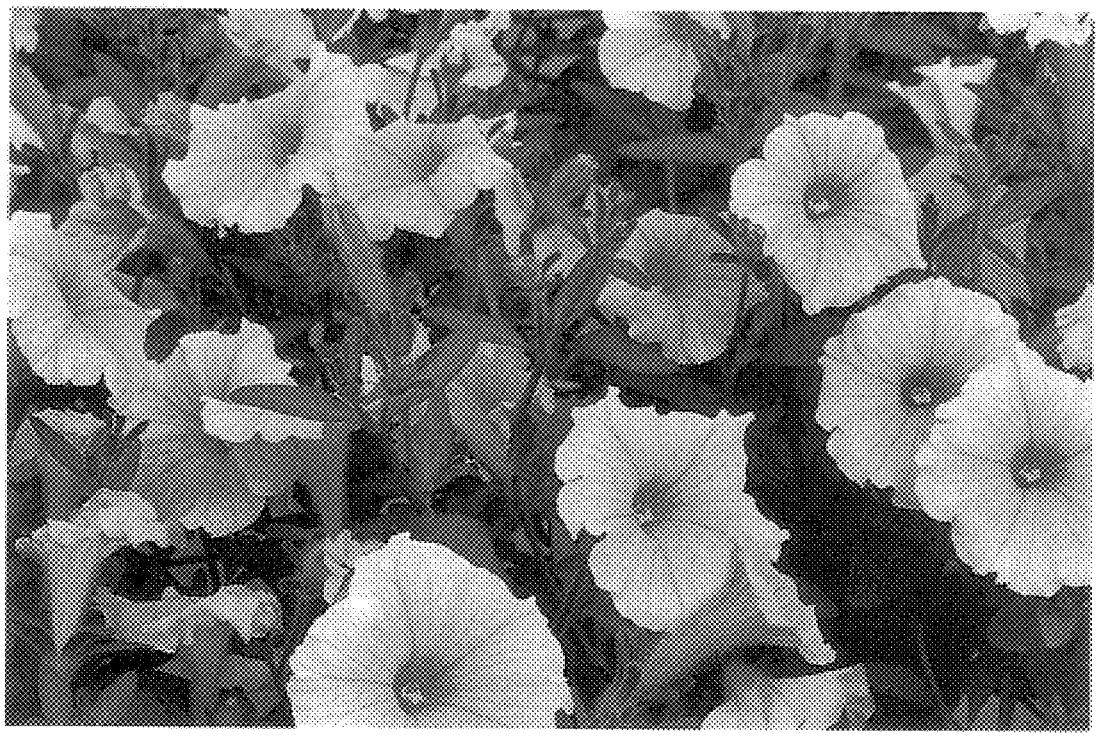

* * * * *